(12) United States Patent
Fujii et al.

(10) Patent No.: US 8,927,289 B2
(45) Date of Patent: Jan. 6, 2015

(54) ATMOSPHERIC CORROSION TEST PROCEDURE AND ITS APPARATUS

(71) Applicant: Hitachi, Ltd., Tokyo (JP)

(72) Inventors: Kazumi Fujii, Hitachi (JP); Katsuhito Takahashi, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 233 days.

(21) Appl. No.: 13/711,719

(22) Filed: Dec. 12, 2012

(65) Prior Publication Data

US 2013/0164852 A1 Jun. 27, 2013

(30) Foreign Application Priority Data

Dec. 27, 2011 (JP) ................................. 2011-284801

(51) Int. Cl.
*G01N 17/00* (2006.01)

(52) U.S. Cl.
CPC .................................... *G01N 17/006* (2013.01)
USPC ................................................ 436/6; 422/53

(58) Field of Classification Search
USPC ................................................ 422/53; 436/6
See application file for complete search history.

(56) References Cited

U.S. PATENT DOCUMENTS

| | | | | |
|---|---|---|---|---|
| 2,405,532 A * | 8/1946 | Todd | | 422/53 |
| 2,521,921 A * | 9/1950 | Kolar, Jr. | | 422/53 |
| 2,523,322 A * | 9/1950 | Ornstein et al. | | 374/57 |
| 2,897,060 A * | 7/1959 | Dieman | | 422/53 |
| 3,098,720 A * | 7/1963 | Neffenger | | 422/53 |
| 3,131,029 A * | 4/1964 | Dieman | | 422/53 |
| 3,163,497 A * | 12/1964 | Gill | | 422/53 |
| 3,259,466 A * | 7/1966 | Jacks, Jr. | | 422/53 |
| 3,273,802 A * | 9/1966 | Hull, Jr. | | 239/338 |
| 3,542,517 A * | 11/1970 | Gill | | 422/53 |
| 3,594,128 A * | 7/1971 | Singleton | | 422/53 |
| 4,069,019 A * | 1/1978 | Suga | | 422/53 |
| 4,092,122 A * | 5/1978 | Suga | | 422/53 |
| 4,114,813 A * | 9/1978 | Suga | | 239/500 |
| 4,689,472 A * | 8/1987 | Singleton et al. | | 392/405 |
| 4,752,446 A * | 6/1988 | Singleton et al. | | 422/53 |
| 4,779,468 A * | 10/1988 | Susuki | | 73/865.6 |
| 4,794,804 A * | 1/1989 | Ishii | | 73/865.6 |

(Continued)

FOREIGN PATENT DOCUMENTS

| | | |
|---|---|---|
| JP | 3834630 B2 | 8/2006 |
| JP | 4218280 B2 | 11/2008 |

(Continued)

*Primary Examiner* — Arlen Soderquist
(74) *Attorney, Agent, or Firm* — Volpe and Koenig, P.C.

(57) ABSTRACT

Provided are an atmospheric corrosion test procedure and an apparatus used for the test. The procedure involves a salt spray step for supplying salt content containing chloride ions on the surfaces of test pieces placed in a thermo-humidistat chamber and a subsequent dry-wet cyclic step including a dry sub-step for drying the surface of the test pieces in the thermo-humidistat chamber at a low relative humidity and a subsequent wet sub-step at a higher relative humidity than that in the dry sub-step, which are cycled. The salt content is supplied by spraying the salt water in the salt spray step. An exhaust step for removing the salt mist sprayed inside thermo-humidistat chamber is further inserted between the salt deposition step and the dry sub-step. The quantity of the salt content deposited on the surfaces of the test pieces is controlled by adjusting the quantity of the sprayed salt water.

14 Claims, 9 Drawing Sheets

(56) References Cited

U.S. PATENT DOCUMENTS

| | | | |
|---|---|---|---|
| 4,995,273 A * | 2/1991 | Kisima et al. | 73/865.6 |
| 5,476,636 A * | 12/1995 | Tomiita et al. | 73/865.6 |
| 5,824,918 A * | 10/1998 | Zuk | 73/865.6 |
| 2013/0109099 A1 * | 5/2013 | Bridenbaker | 436/6 |

FOREIGN PATENT DOCUMENTS

| | | |
|---|---|---|
| JP | 2010-025560 A | 2/2010 |
| JP | 2010-085144 A | 4/2010 |
| JP | 2011-069625 A | 4/2011 |
| JP | 2012-026945 A | 2/2012 |

* cited by examiner

F I G . 3
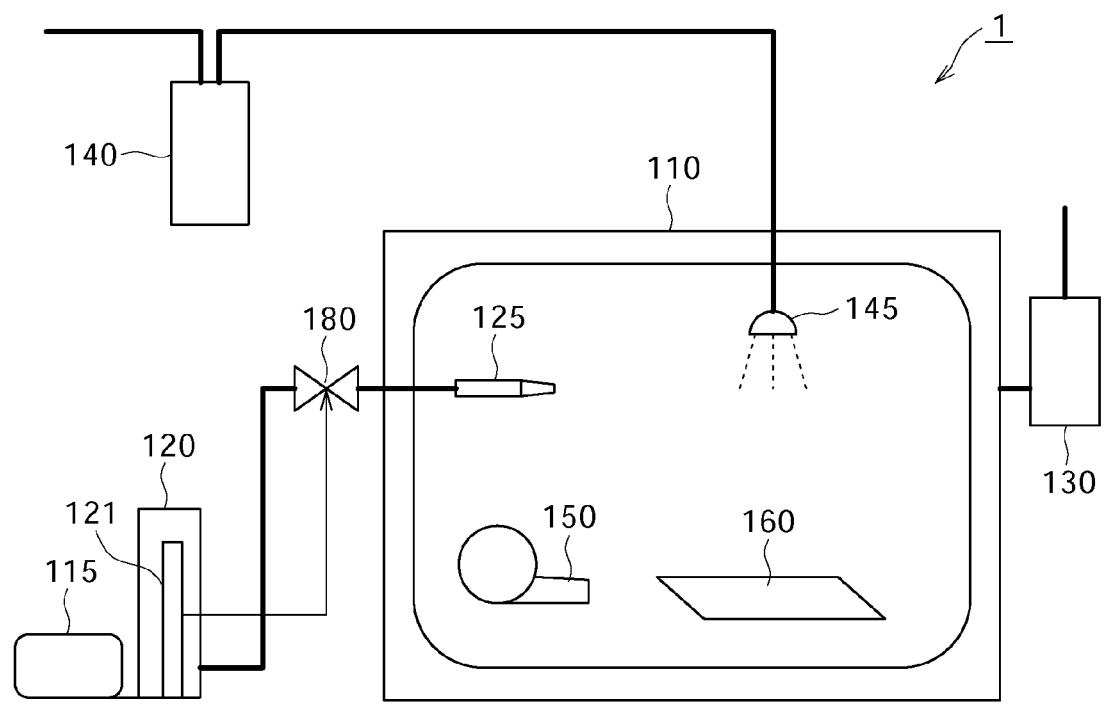

F I G . 4
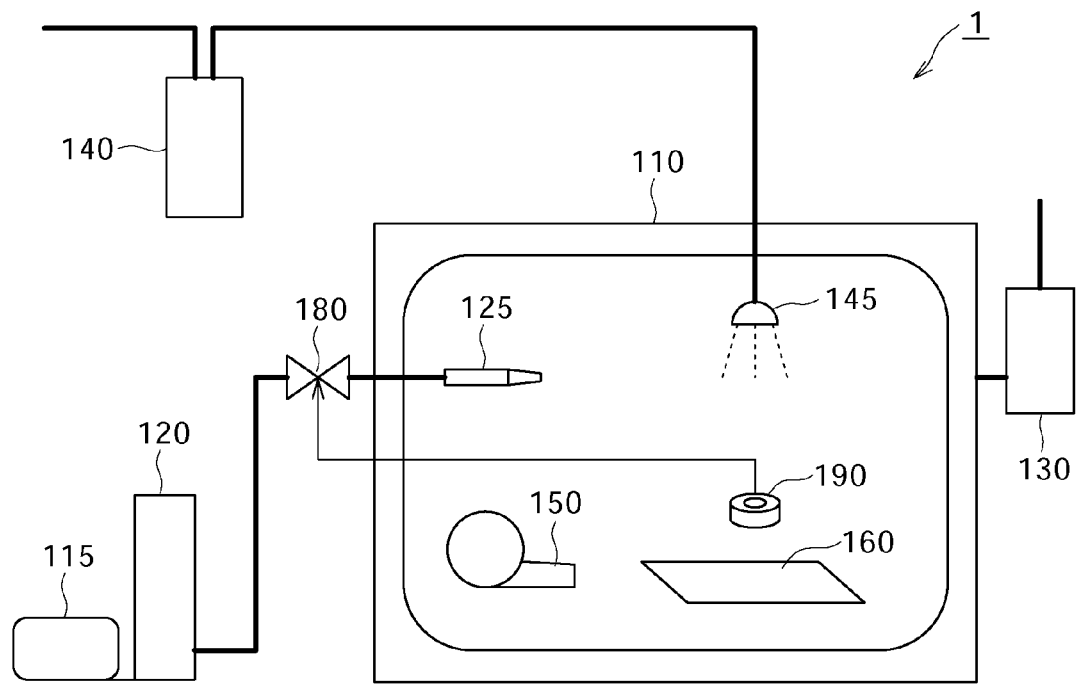

_US 8,927,289 B2_

ATMOSPHERIC CORROSION TEST PROCEDURE AND ITS APPARATUS

FIELD OF THE INVENTION

The present invention relates to an atmospheric corrosion test procedure for metallic materials and its apparatus.

BACKGROUND OF THE INVENTION

A salt spray test defined in JIS Z 2371 and a cyclic corrosion test defined in JIS K 5600-7-9 have been known for the tests for evaluating the corrosion resistance of metallic materials used in the atmosphere.

Japanese Patent No. 4218280 also discloses a corrosion test procedure carried out in the simulated corrosion environment, to which test pieces are actually exposed, by adjusting the test conditions, such as the quantity of salt content to be deposited on the test pieces, and the temperature and relative humidity. The corrosion test procedure disclosed in Japanese Patent No. 4218280 involves a step of depositing a given quantity of salt content on the test pieces and a subsequent dry-wet cyclic step, in which a dry state and a wet state are cycled in preset temperature and relative humidity conditions. Both of these steps are repeated. According to the corrosion test procedure of the present invention, salt water adjusted to a given concentration is used as a chemical substance for accelerating corrosion and salt mist is sprayed on the test pieces to deposit salt content on the surfaces thereof.

On the other hand, Japanese Patent No. 3834630 discloses a corrosion test procedure, in which fine sea salt particles are formed by generating air bubbles in sea water.

SUMMARY OF THE INVENTION

As disclosed in Japanese Patent No. 4218280, the adjustment of the test conditions has enabled the actual states of corrosion of metallic materials in their service conditions to be reproduced, considerably improving an accuracy in evaluation of corrosion resistance, compared with the test procedures according to the prior art. However, when the salt mist is sprayed on the test pieces, the droplets of the sprayed salt mist, which is deposited and agglomerated on the test pieces, wet the surfaces thereof, leading to a considerable difference in size from the sea salt particle coming flying in the natural environment (about dozens of μm). Thus, the above-mentioned salt spray procedure, in which saltwater is simply sprayed on the test pieces to deposit the salt particles on the surface thereof, has a problem to be solved that it can not satisfactorily reproduce corrosion caused due to the deposition of salt particles coming flying in the natural environment.

As disclosed in Japanese Patent No. 3834630, the salt deposition step, in which air bubbles are generated in sea water, is suitable for the test conducted in such a manner that corrosion is accelerated while salt particles are being deposited at a low speed; however, it causes a problem in the test conducted in such a manner that a dry-wet cyclic step of cycling between the dry state and the wet state is separated from a salt deposited step as disclosed in Japanese Patent No. 4218280, in that the salt deposition step requires long time, during which corrosion is excessively accelerated.

Furthermore, both the procedures according to the prior art disclosed in Japanese Patent No. 4218280 and Japanese Patent No. 3834630 have such a problem that when the salt deposition step is repeated, the quantity of the salt content deposited on the test pieces vary among the individual salt deposition steps, causing deteriorated reproducibility in the corrosion test.

An object of the present invention is to reduce a variation in the quantity of salt deposited on the test pieces, achieving the improved reproducibility of corrosion in the atmospheric corrosion test.

The test procedure according to the present invention involves a salt deposition step for supplying salt content containing chloride ions on the surfaces of test pieces placed in a thermo-humidistat chamber, and a subsequent dry-wet cyclic step including of a dry sub-step for drying the surfaces of the test pieces in the thermo-humidistat chamber at a low relative humidity, and a subsequent wet sub-step for wetting the surfaces of the test pieces at a higher relative humidity than that of the dry sub-step. These two sub-steps are cycled more than one time. Herein, the salt content is supplied by spraying saltwater on the test piece in the salt deposition step, an exhaust step of removing the salt mist sprayed inside the thermo-humidistat chamber is carried out between the salt deposition step and the dry sub-step, and the quantity of the salt content deposited on the surfaces of the test pieces is controlled by adjusting the quantity of sprayed salt water.

According to the present invention, the corrosion caused due to the deposition of sea salt particles coming flying in the natural environment may be reproduced and a variance in quantity of the salt content deposited on the surfaces of the test pieces may be also reduced in the atmospheric corrosion test involving the repeated salt deposition step, achieving the improved test accuracy.

BRIEF DESCRIPTION OF THE DRAWING

FIG. 3 is another block diagram of the atmospheric corrosion test apparatus according to the embodiment 3 of the preset invention;

FIG. 4 is a block diagram of the atmospheric corrosion test apparatus according to an embodiment 4 of the present invention;

DETAILED DESCRIPTION OF THE PREFERRED EMBODIMENTS

Figure 1:
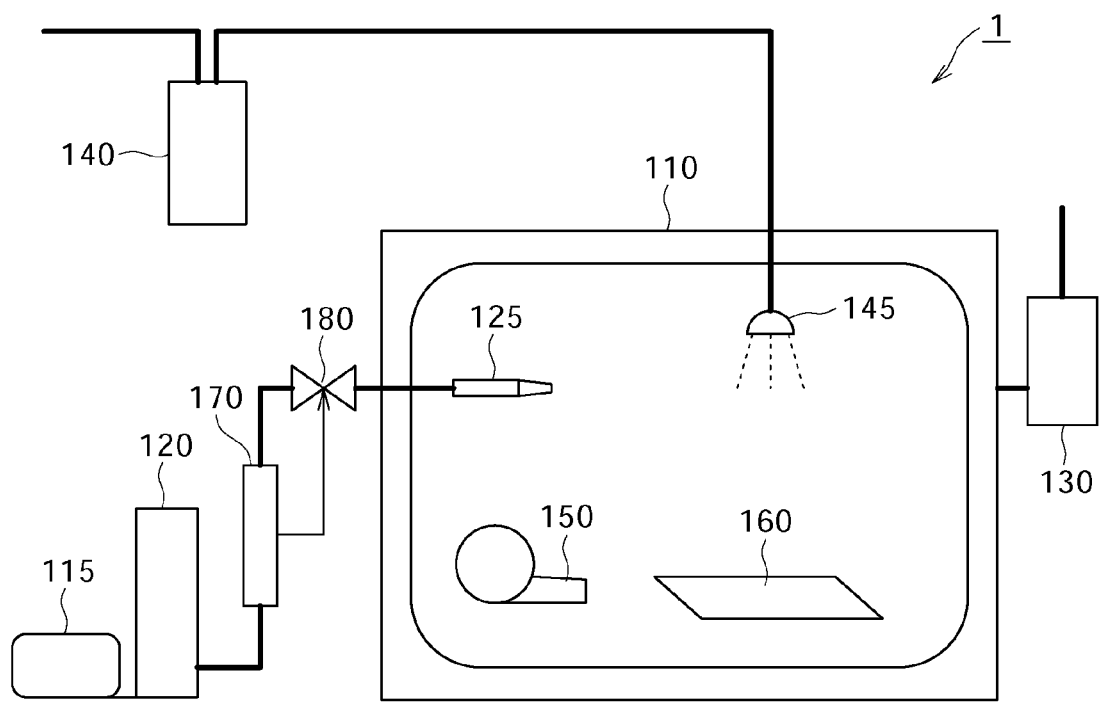
FIG. 1 is a block diagram of an atmospheric corrosion test apparatus according to an embodiment 3 of the preset invention.

The present invention relates to a corrosion test procedure for metallic materials used for office automation equipment (copiers, personal computers, etc.), audiovisual devices (TV sets, video equipment, etc.), home appliances such as refrigerators, washing machines, etc., industrial electric equipment/machinery such as controllers, generators, etc., and transport equipment such as automobiles and vehicles, as well as used for the parts assembled in these electric equipment and machines.

Hereinafter, an atmospheric corrosion test procedure and its apparatus of the present invention are described in detail.

The atmospheric corrosion test procedure involves a salt deposition step of supplying salt content containing chloride ions on the surfaces of test pieces placed in a thermo-humidistat chamber, and a subsequent dry-wet cyclic step. The dry-wet cyclic step includes a dry sub-step of drying the surfaces of the test pieces in the thermo-humidistat chamber at a low relative humidity and a subsequent wet sub-step of wetting them in the thermo-humidistat chamber at a higher relative humidity than that in the dry sub-step. The dry sub-step and the wet sub-step are cycled more than one time. The salt content is supplied by spraying salt mist onto the surfaces of the test pieces, the first one of the repeated dry sub-steps is carried out between the first one of the repeated dry sub-steps subsequently to the salt spray step and a first one of the repeated wet sub-steps, and the salt mist sprayed inside the thermo-humidistat chamber is removed in an exhaust step carried out between the first dry sub-step subsequent to the salt deposition step and the first one of the repeated wet sub-steps, and the quantity of the salt content deposited on the surfaces of the test pieces is controlled by adjusting the quantity of the sprayed salt mist.

Herein, the first dry sub-step is the first dry sub-step of a dry-wet cyclic step consequent to the salt deposition step. A wet sub-step carried out directly after the first dry sub-step is the first wet sub-step.

In the atmospheric corrosion test procedure, the dry sub-step is preferably started by varying stepwisely the temperature and relative humidity inside the thermo-humidistat chamber starting from the salt deposition step or the wet sub-step.

In the atmospheric corrosion test procedure, the quantity of the sprayed salt mist is preferably adjusted to the values obtained by measuring the mass or volume of the salt water.

In the above-mentioned atmospheric corrosion test procedure, the mass or volume of the salt water is preferably measured with time and controlled to stop the salt spray step when it reaches a preset value thereof.

In the atmospheric corrosion test procedure, the salt deposition step is preferably carried out in an ambient atmosphere in any one of conditions combining a temperature selected from a range from 0 to 60° C. and a relative humidity selected from a range from 10 to 98%.

In the atmospheric corrosion test procedure, it is preferable that the procedure is cyclically gone back to the salt deposition step subsequent to the dry-wet cyclic step and further to the dry-wet cyclic step.

In the atmospheric corrosion test procedure, it is preferable that a rinsing step of removing the salt content deposited on the surfaces of the test pieces with rinsing water is carried out between the dry-wet cyclic step and the subsequent salt deposition step.

In the atmospheric corrosion test procedure, it is preferable that one cycle including one salt deposition step and one dry-wet cyclic step is repeated every day or at the intervals of one to six days; namely the duration of one cycle preferably lies within a range from one to six days.

In the atmospheric corrosion test procedure, it is preferable that the dry sub-step includes a sub-step of measuring the mass of the salt content remaining on the surfaces of the test pieces after water content is removed therefrom.

The atmospheric corrosion test apparatus has a thermo-humidistat chamber for placing the test pieces, a saltwater reservoir for storing the salt water supplied inside the thermo-humidistat chamber, a salt mist supplying unit for generating salt mist, an exhaust unit for collecting the mist from inside the thermo-humidistat chamber and exhausting it, a flow rate measuring unit for measuring the quantity of supplied salt mist or an deposited salt measuring unit for measuring the quantity of the salt water deposited on the surfaces of the test pieces, and a control unit for adjusting the quantity of the supplied salt mist based on a signal issued from the flow rate measuring unit or the deposited salt measuring unit.

It is preferable that the atmospheric corrosion test apparatus further has a rinsing nozzle for spreading the rinsing water on the test pieces and a warm-air drying unit for removing the rinsing water deposited on the surfaces of the test pieces.

In the atmospheric corrosion test apparatus, the exhaust unit has preferably a function for varying stepwisely the temperature and relative humidity inside the thermo-humidistat chamber.

It is preferable that the atmospheric corrosion test apparatus further has an on-off valve for adjusting the quantity of the supplied salt mist between the saltwater reservoir and the salt mist generator.

In the atmospheric corrosion test apparatus, the control unit controls preferably the on-off valve based on the signal issued from the deposited salt measuring unit.

Hereinafter, the present invention will be described in detail by way of typical embodiments with reference to the drawings.

DETAILED DESCRIPTION OF THE PREFERRED EMBODIMENTS

First Embodiment

Figure 7:
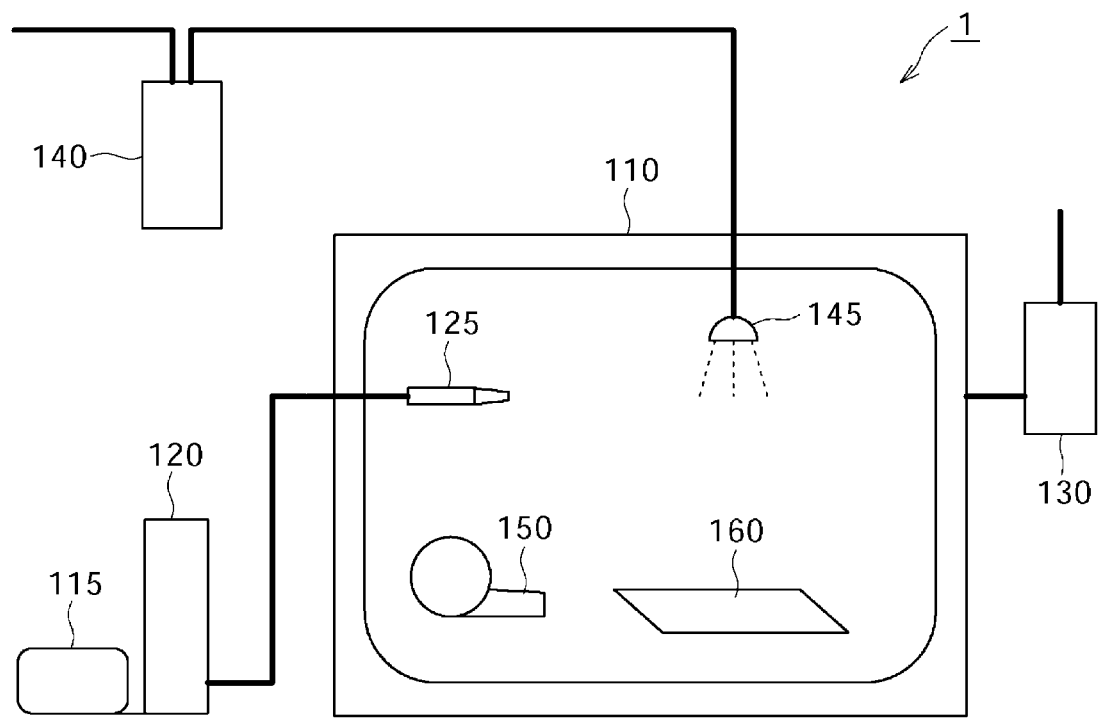
FIG. 7 is a block diagram of the atmospheric corrosion test apparatus according to an embodiment 1 of the preset invention.

FIG. 7 is a block diagram of an atmospheric corrosion test apparatus, which automatically carries out a series of steps of an atmospheric corrosion test procedure.

The atmospheric corrosion test apparatus 1 is composed of a thermo-humidistat chamber 110, a pump 115, a salt-water tank 120 (salt-water reservoir), a salt-water nozzle 125 (salt mist supplying unit), an exhaust unit 130, a rinsing water tank 140, a rinsing water nozzle 145, and a warm-air drying unit 150. Inside the thermo-humidistat chamber 110, a space is left for placing the test pieces 160. This figure shows the thermo-humidistat chamber 110 with the test piece 160 placed therein. The thermo-humidistat chamber 110 further has the salt-water nozzle 125, the rinsing water nozzle 145, and a warm-air drying unit 150 therein.

The thermo-humidistat chamber 110 also has a programming function capable of controlling independently the temperature and relative humidity therein and continuously varying among more than one of test conditions combining the selected temperature and relative humidity. It further has a function capable of controlling the temperature and relative humidity while introducing the outside air.

The exhaust unit 130 removes the salt mist from inside the thermo-humidistat chamber 110. For the exhaust unit 130, an exhaust system capable of collecting the removed salt mist and exhausting only the air is used. The exhaust unit 130 exhausts forcibly the air staying inside the thermo-humidistat chamber 110 outward, as well as collects the salt mist (salt mist). The salt mist is collected using a baffle plate, a meshed filter, a cyclone, etc.

The warm-air drying unit 150 blows warm air onto the test pieces 160 to remove the remaining rinsing water therefrom.

The test piece 160 made of a material used to evaluate corrosion resistance is placed with the evaluation side thereof facing upward. In this embodiment, a galvanized steel sheet formed into the shape 70×70×1 mm was used for the test pieces 160.

The salt water is stored in the salt-water tank 120 and subsequently, supplied onto the test pieces 160 placed in the thermo-humidistat chamber 110 as the salt mist (salt mist) from the salt nozzle 125 by means of power of the pump 115. This configuration allows the salt content to be deposited on the test pieces 160.

3.5% concentration of artificial seawater was used for the salt water. The artificial sea water was obtained by dissolving Aquamarine (registered trademark, YASHIMA) in water.

The quantities of the components of the artificial sea water (quantities of individual reagents in 20 L of water) are NaCl: 490.68 g, $MgCl_2 \cdot 6H_2O$: 222.23 g, $Na_2SO_4$: 81.88 g, $CaCl_2 \cdot 2H_2O$: 30.70 g, KCl: 13.89 g, $NaHCO_3$: 4.02 g, KBr: 2.01 g, $H_3BO_3$: 0.54 g, NaF: 0.06 g, and $SrCl_2 \cdot 6H_2O$: 0.85 g.

Pure water is used for the rinsing water. The rinsing water stored in the rinsing water tank 140 is spread on the test pieces 160 from the rinsing water nozzle 145 to remove the salt content deposited on the surfaces of the test pieces 160.

Hereinafter, the steps of the atmospheric corrosion test procedure of the present invention will be described.

Figure 8:
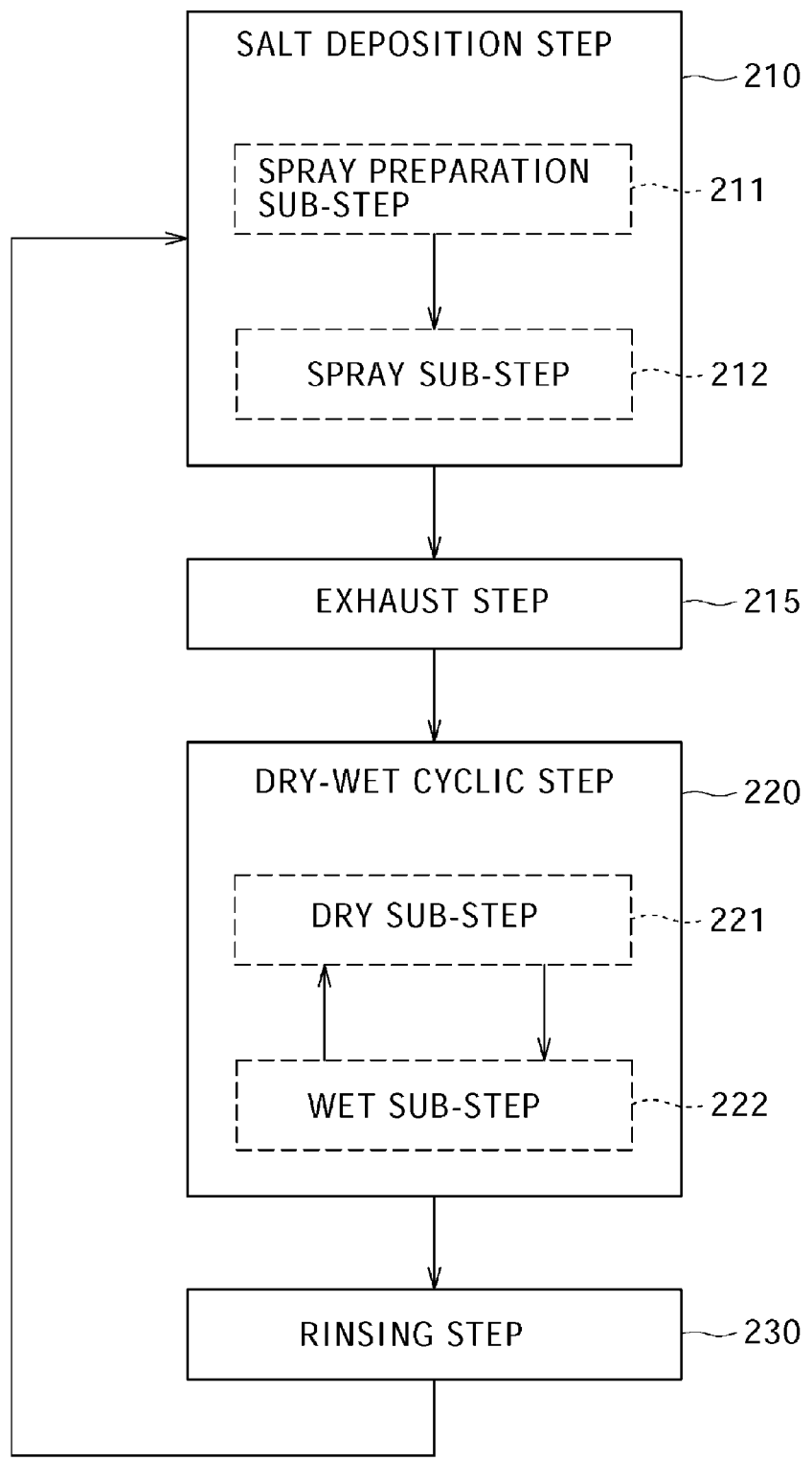
FIG. 8 is a flow sheet illustrating the steps of the atmospheric corrosion test procedure according to the embodiment 1 of the present invention.

FIG. 8 shows the steps of the atmospheric corrosion test procedure of the present invention.

In this figure, the atmospheric corrosion test procedure of the present invention involves the salt deposition step 210, the exhaust sub-step 215, the dry-wet cyclic step 220, and the rinsing step 230. The salt deposition step 210 further includes a spray preparation sub-step 211 and a spray sub-step 212, and in the dry-wet cyclic step 220, the dry sub-step 221 and the wet sub-step 222 are cycled in a given cycle.

In the atmospheric corrosion test procedure according to this embodiment, the salt deposition step 210, the dry-wet cyclic step 220, and the rinsing step 230 were repeated in the given cycle. Specifically, the dry-wet cyclic step 220 carried out for four weeks, during which the salt deposition step 210 and the rinsing step 230 were carried out twice a week. In other words, these steps are sequentially repeated out as follows: the first salt deposition step 210; the dry-wet cyclic step 220 for about three days; the rinsing step 230; the second salt deposition step 210; the second dry-wet cyclic step 220 for about three days; the second rinsing step 230; the third salt deposition step 210, the third dry-wet cyclic step 220 for about three days, all of which are repeated.

In the spray preparation sub-step 211, the thermo-humidistat chamber 110 was operated to make the temperature and relative humidity therein constant. In this embodiment, the temperature and relative humidity were set to 40° C.±1° C. and 35% RH±3%, respectively. Since the preliminary examination had shown that the temperature and relative humidity became constant 20 minutes after the start of operation, the thermo-humidistat chamber 110 was operated for 30 minutes or more, longer than the time duration obtained from the preliminary examination on the safe side.

In the spray sub-step 212, the salt water nozzle 125 generated salt mist and spread onto the test pieces 160 to deposit the salt content on the surfaces thereof. Since the preliminary examination had also shown that the quantity of the deposited salt content increases proportionally to a spray time, the spray time was set to 12 minutes to deposit 1 g of salt content per 1 $m^2$ in this embodiment. Directly after the spray sub-step 212, the salt mist remaining inside the thermo-humidistat chamber 110 continues to deposit the surfaces of the test pieces 160.

Since the deposition of the remaining salt mist on the surfaces of the test pieces 160 causes a variance in quantity of the deposited salt content, immediately after the spray sub-step 212, the exhaust sub-step 215 for operating the exhaust unit 130 was carried out to remove the salt mist remaining inside the thermo-humidistat chamber 110. When one of the test pieces 160 was taken out and the particles of the deposited salt content were observed, the average size of the particles of the salt content was 25 μm. The operation of the exhaust unit 130 immediately after the spray sub-step 212 enables the temperature and relative humidity inside the thermo-humidistat chamber 110 to be varied stepwisely.

In the subsequent dry-wet cyclic step 220, the dry sub-step 221 and the wet sub-step 222 were cycled on the test pieces 160 with the salt content deposited thereon. In this embodiment, one cycle was set to 8 hours.

In other words, in the dry sub-step 221, the temperature and relative humidity inside the thermo-humidistat chamber 110, and the retention time were set to 60° C., 35%, and three hours, respectively and in the wet sub-step 222, the temperature and relative humidity inside the thermo-humidistat chamber 110, and the retention time were set to 40° C., 95%, and three hours, respectively. Each of the transition times from the dry sub-step 221 to the wet sub-step 222 and from the wet sub-step 222 to the dry sub-step 221 was set to one hour.

As described herein, the first dry sub-step 221 is the first dry sub-step of the dry-wet cyclic step 220 subsequently to the salt deposition step 210. The wet sub-step 222 directly subsequently to the first dry sub-step 221 is the first wet sub-step.

The comparison of the test results obtained from the corrosion test procedure according to this embodiment of the present invention with those obtained in the actual environment demonstrated that corrosion behavior was identical between both the test and actual environments.

Second Embodiment

Figure 9:
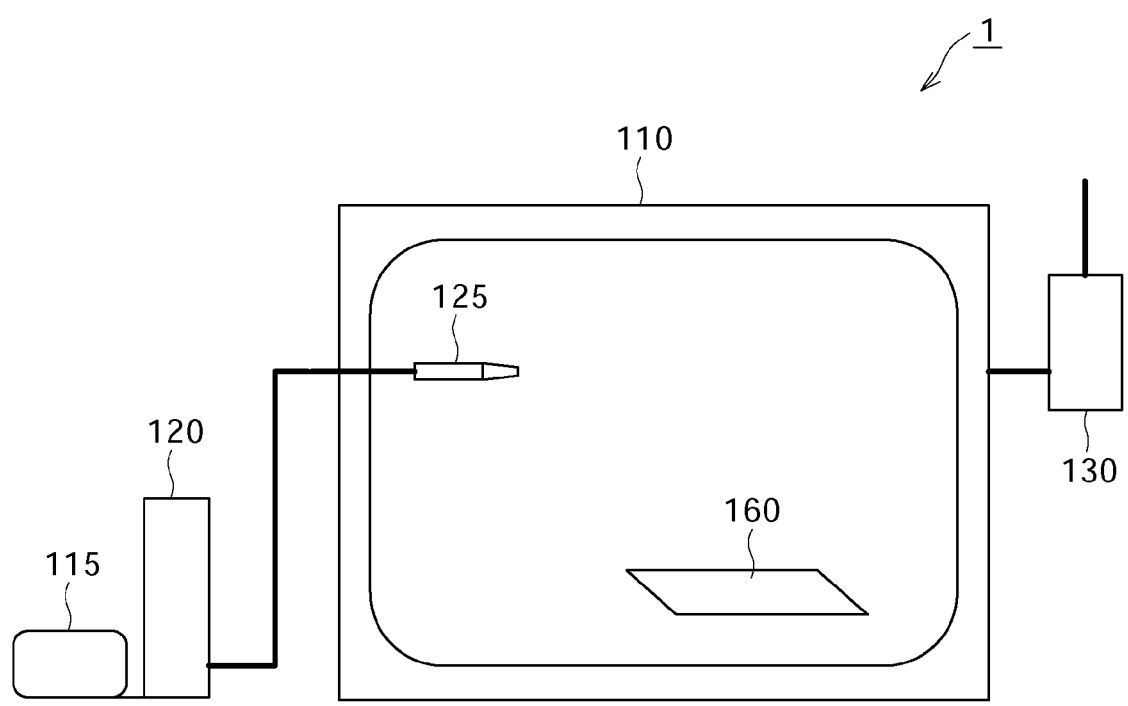
FIG. 9 is a block diagram of the atmospheric corrosion test apparatus according to an embodiment 2 of the preset invention.

FIG. 9 is a block diagram of a semi-automatic apparatus carrying out the atmospheric corrosion test procedure, in which only the rinsing step is carried out manually and other steps are carried out automatically.

The atmospheric corrosion test apparatus 1 is composed of the thermo-humidistat chamber 110, the pump 115, the salt water tank 120 (salt water reservoir), the salt-water nozzle 125 (salt mist supplying unit), and the exhaust unit 130. The atmospheric corrosion test apparatus according to the second embodiment is different from the apparatus according to the first embodiment in that it does not include the rinsing water tank 140, the rinsing water nozzle 145, and the warm-air drying unit 150.

In this embodiment, an aluminum alloy sheet formed into the shape 70×70×3 mm was used for the test pieces 160.

Next, the atmospheric corrosion test procedure according to this embodiment will be described with reference to FIG. 8. The explanation described in the first embodiment will be partially omitted and thereinafter, differences of the atmospheric corrosion test procedure according to the second embodiment from the procedure according to the first embodiment will be mainly described.

In the atmospheric corrosion test procedure according to this embodiment, the dry-wet cyclic step 220 was carried out for 12 weeks, the test pieces 160 were took out from the thermo-humidistat chamber 110 twice a week, and then the rinsing step 230 was carried out.

In the spray preparation sub-step 211, the thermo-humidistat chamber 110 was operated to make the temperature and relative humidity constant. In this embodiment, the thermo-humidistat chamber 110 was operated for 30 minutes or more to make the temperature and relative humidity therein constant. In this embodiment, the salt content was deposited on the test pieces 160 in such a condition a that the temperature and relative humidity retained in the spray preparation sub-step 211 might be 40° C.±1° C. and 35% RH±3%, respectively. For comparison, the salt content was also deposited on the test pieces 160 in such a condition b that the temperature and relative humidity might be 40° C.±1° C. and 65% RH±3%, respectively and in such a condition c that they might be 40° C.±1° C. and 95% RH±3%, respectively.

In the spray sub-step 212, the salt mist was generated to deposit on the test pieces 160. Since the preliminary examination had shown that the quantity of the deposited salt content increases proportionally to the spray time, the spray time was set to 12 minutes to deposit 1 g of salt content per 1 m².

The exhaust unit 130 was operated immediately after the spray sub-step 212 to remove the salt mist remaining inside the thermo-humidistat chamber 110. The salt deposition step 210 was carried out in each of the conditions a, b, and c to obtain the test pieces 160a, 160b, and 160c, respectively, all of which had the salt content deposited thereon. The average diameter of the salt particles deposited on the test piece obtained in the condition a was 25 μm. The average diameters of the salt particles deposited on the test pieces obtained in the conditions a and b were 50 μm and 100 μm, respectively.

Thus, it was verified that selecting the temperature and relative humidity might vary the size of the particles of the deposited salt content.

Subsequently, in the dry-wet cyclic step 220, the dry sub-step 221 and the wet sub-step 222 were cycled on the test pieces 160 with the salt content deposited thereon. One cycle was set to eight hours in this embodiment.

In the dry sub-step 221, the temperature and relative humidity inside the thermo-humidistat chamber 110, and the retention time were set to 35° C., 40%, and one hour, respectively and in the wet sub-step 222, they were set to 20° C., 95%, and one hour, respectively. Each of the transition times from the dry sub-step 221 to the wet sub-step 222 and from the wet sub-step 222 to the dry sub-step 221 was set to one hour.

In the rinsing step 230, the test pieces 160 were took out from the thermo-humidistat chamber 110 twice a week and rinsed with pure water to rinse away the deposited salt content. After rinsing with water, the rinsing water remaining on the test pieces 160 was removed by a warm-air dryer and then the salt deposition step 210 was carried out.

Twelve weeks after the start of the test, the test pieces 160a, 160b, and 160c were collected and the progress of corrosion compared among them.

On the test piece 160a, faint metallic luster stayed and corrosion with white corrosion products in spots was observed.

As with the test piece 160a, on the test piece 160b, faint metallic luster stayed and corrosion with white corrosion products in spots was observed. The corrosion with white corrosion products observed on the test piece 160b was larger than that observed on the test piece 160a; however, the test piece 160b had a tendency to corrode similar to that of the test piece 160a.

On the test piece 160c, a part which metallic luster stayed with no corrosion was clearly different from a part which had been corroded with white corrosion products. The corrosion behavior on the test piece 160c was evidently different from those on the test pieces 160a and 160b.

The comparison among test pieces 160a, 160b, and 160c with those obtained in the actual environment demonstrated that the corrosion behavior of the test piece 160a was similar to those obtained in the actual environment and the corrosion behavior of the test piece 160c was evidently different from them.

Third Embodiment

FIG. 1 is a block diagram of an apparatus automatically carrying out a series of steps of the atmospheric corrosion test procedure.

As known from this figure, the quantity (volume) of the salt mist supplied from the salt-water nozzle 125 is measured using an integrating flowmeter 170 (flow rate measuring unit) and closing an on-off valve 180 when the volume reaches a preset value to stop the spray of salt water. A rinsing water tank 140 and a warm-air drying unit 150 have been incorporated inside the thermo-humidistat chamber 110. This figure shows the apparatus according to this embodiment with test pieces 160 placed therein.

The explanation described in the first embodiment will be partially omitted and thereinafter, differences of the apparatus according to the third embodiment from the apparatus according to the first embodiment will be mainly described.

As with the first embodiment, the thermo-humidistat chamber 110 according to this embodiment is capable of controlling independently the temperature and relative humidity therein and provides a programming function for continuously varying among more than one of conditions combining the selected temperature and relative humidity.

In this embodiment, ion-exchanged water was used for the rinsing water. The warm-air drying unit 150 blows warm air onto the test pieces 160 to remove the remaining rinsing water.

In this embodiment, a galvanized steel sheet formed into the shape 70×70×1 mm was used for the test pieces 160.

Prior to an actual corrosion test, first, the test conditions of the temperature and relative humidity inside the thermo-humidistat chamber 110, and the volume of the sprayed salt content for depositing the salt particles of a given size are found. In this embodiment, assuming that the size of the salt particles deposited on the surface of the galvanized steel sheet was about 20 μm at the center and the quantity of the salt content deposited was 1 g/m², the temperature, relative humidity, and the volume of the sprayed salt content were set to 40° C., 35%, and 50 ml, respectively.

Figure 2:
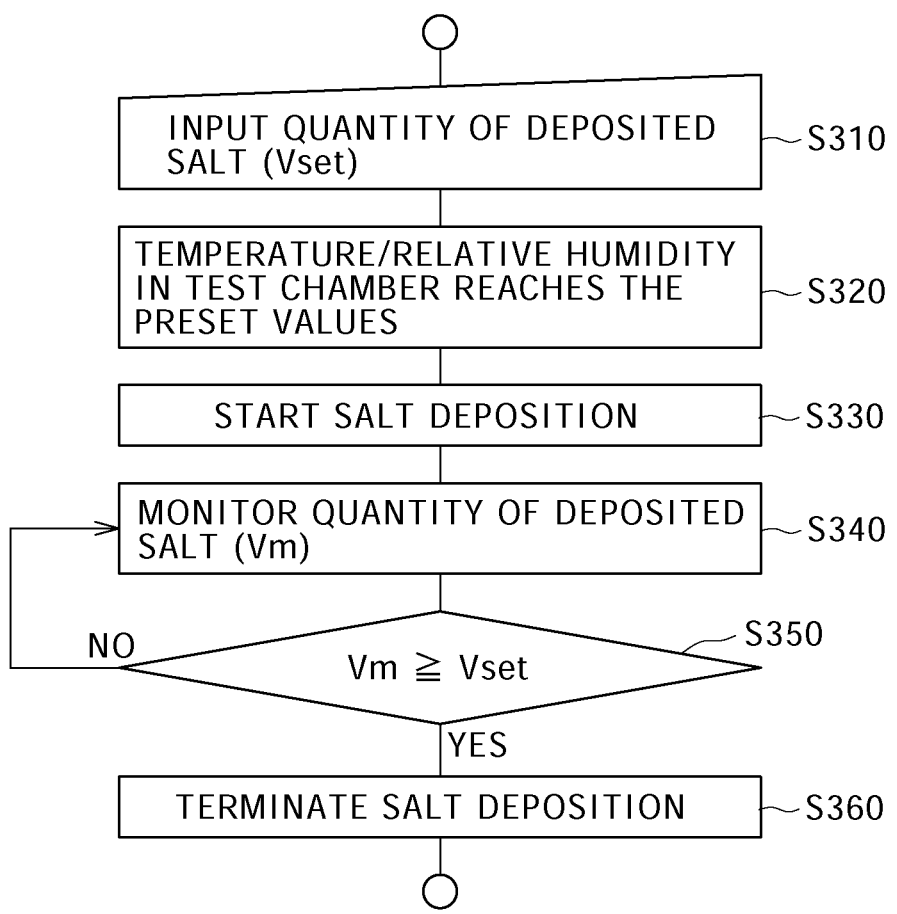
FIG. 2 is a flow sheet illustrating the steps of an atmospheric corrosion test procedure according to the embodiment 3 of the present invention.

The salt deposition step of the atmospheric corrosion test procedure according to this embodiment based on the above-mentioned conditions is shown in FIG. 2.

In the salt deposition step, first, the previously-found quantity of the deposited salt content is entered in a control unit of the test apparatus. In this case, $V_{set}$ was set to 50 ml for the quantity of the deposited salt content (S310). In the actual step of depositing the salt content, when it is sensed that the temperature and relative humidity inside the thermo-humidistat chamber have reached 40° C. and 35%, respectively (S320), the on-off valve is opened to start the deposition of the salt content (S330). Then, the measurement of the volume $V_m$ of the salt water is started using an integrating flowmeter (S340) concurrently with the start of deposition of the salt content to monitor the quantity of the deposited salt content and determine whether $V_m$ has reached the preset $V_{set}$ value (S350). When $V_m$ reaches $V_{set}$, the on-off valve 180 is closed to end the deposition of the salt content (S360).

It was verified that repeating the procedure shown in this figure enabled a variance in quantity of the deposited salt content to be suppressed, improving the reproducibility of corrosion in the corrosion test.

FIG. 3 is a block diagram of a variation of a test apparatus according to this embodiment.

The basic configuration of the atmospheric corrosion test apparatus 1 is as shown in this figure, however, a saltwater tank water level indicator 121 (deposited salt water measuring unit) has been incorporated in the salt water tank 120. In this configuration, the volume of the salt mist is measured based on a variation indicated on the salt water tank water level indicator 121 and the on-off valve 180 is closed when the measured volume reaches the preset value to stop the spray of the salt water.

Even if the atmospheric corrosion test apparatus 1 configured as shown in this figure was used, the deposition of the salt content might be controlled based on the measured volume of the salt water as shown in this embodiment to suppress a variance in quantity of the deposited salt content among the salt deposition steps, improving the reproducibility of corrosion in the corrosion test.

Fourth Embodiment

FIG. 4 is a block diagram of an apparatus automatically carrying out a series of steps of the atmospheric corrosion test procedure.

The configuration of the apparatus shown in this figure is different from that shown in FIG. 1 in that the mass of the salt mist deposited on the test pieces 160 is measured using a quartz crystal microbalance sensor 190 (deposited salt measuring unit) installed adjacently to the test pieces 160 and when the measured mass value reaches the preset mass value, the on-off valve 180 is closed to stop the spray of the salt water.

The thermo-humidistat chamber 110 is capable of controlling individually the temperature and relative humidity therein and provides the programming function for continuously varying among more than one of test conditions combining the selected temperature and relative humidity.

In this embodiment, ion-exchanged water was used for the rinsing water. The warm-air drying unit 150 blows warm air onto the test pieces 160 to remove the remaining rinsing water.

In this embodiment, an aluminum die casting sheet formed into the shape 70×70×3 mm was used for the test pieces 160.

First, the test conditions of the temperature and relative humidity inside the thermo-humidistat chamber 110, and the volume of the sprayed salt content for depositing a given quantity of salt particles of a given size is found. In this embodiment, assuming that the size of the salt particles deposited on the surface of the aluminum die casting sheet was about 35 μm at the center, the temperature and relative humidity were set to 65° C. and 65%, respectively.

Figure 5:
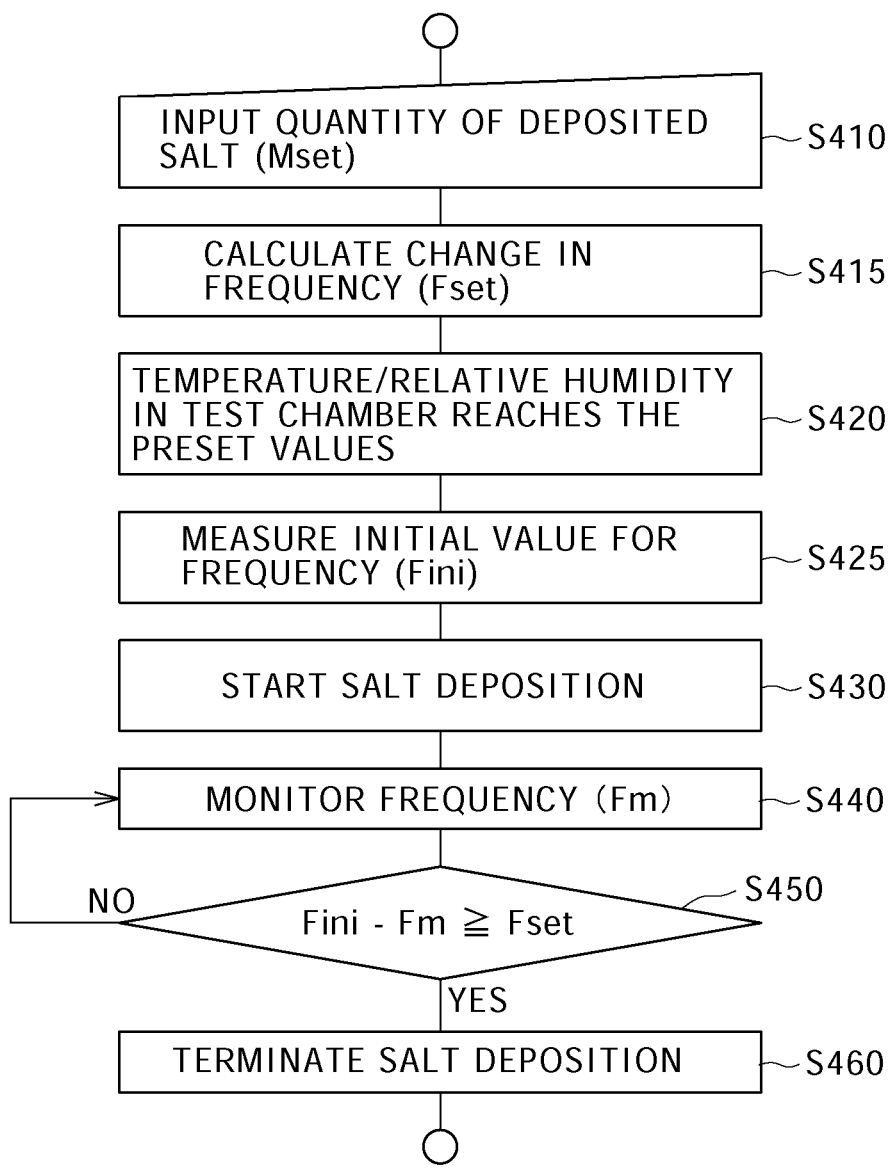
FIG. 5 is a flow sheet illustrating the steps of the atmospheric corrosion test procedure according to the embodiment 4 of the present invention.

The salt deposition step of the atmospheric corrosion test procedure according to this embodiment based on the above-mentioned condition is shown in FIG. 5.

In the salt deposition step, first, the previously-found quantity of the deposited salt content is entered in a control unit of the test apparatus. In this case, $M_{set}$ was set to 0.1 g/m² for the quantity of the deposited salt content (S410). A change in frequency $F_{set}$ (Hz) on the quartz crystal microbalance sensor 190, which is equivalent to the quantity of the deposited salt content, is calculated (S415). In the actual step of depositing the salt content, when it is sensed that the temperature and relative humidity inside the thermo-humidistat chamber have reached 65° C. and 65%, respectively (S420), the initial value $F_{ini}$ (Hz) for the frequency on the quartz crystal microbalance sensor 190 is measured (S425).

Then, the on-off valve 180 is opened to start the deposition of the salt content (S430). The measurement of the frequency $F_m$ for the quartz crystal microbalance sensor 190 is started concurrently with the start of the deposition of the salt content, the quantity of the deposited salt content is monitored (S440), and a change in frequency is calculated by evaluating a formula $F_{ini}-F_m$ to determine whether the obtained value has reached the preset $F_{set}$ (Hz) (S450). When $F_{ini}-F_m$ reaches $F_{set}$, the on-off valve 180 is closed to end the deposition of the salt content (S460).

It was verified that repeating the procedure shown in this figure enabled a variance in quantity of the deposited salt content to be suppressed among the salt spray steps, improving the reproducibility of the corrosion test.

It should be noted that in this embodiment, the quartz crystal microbalance sensor 190 was used for the deposited salt content measuring unit but the present invention is not limited to this sensor and any type of sensor capable of measuring the quantity of the salt content deposited on the test pieces 160 may be used regardless of the measuring mode thereof.

Fifth Embodiment

Figure 6:
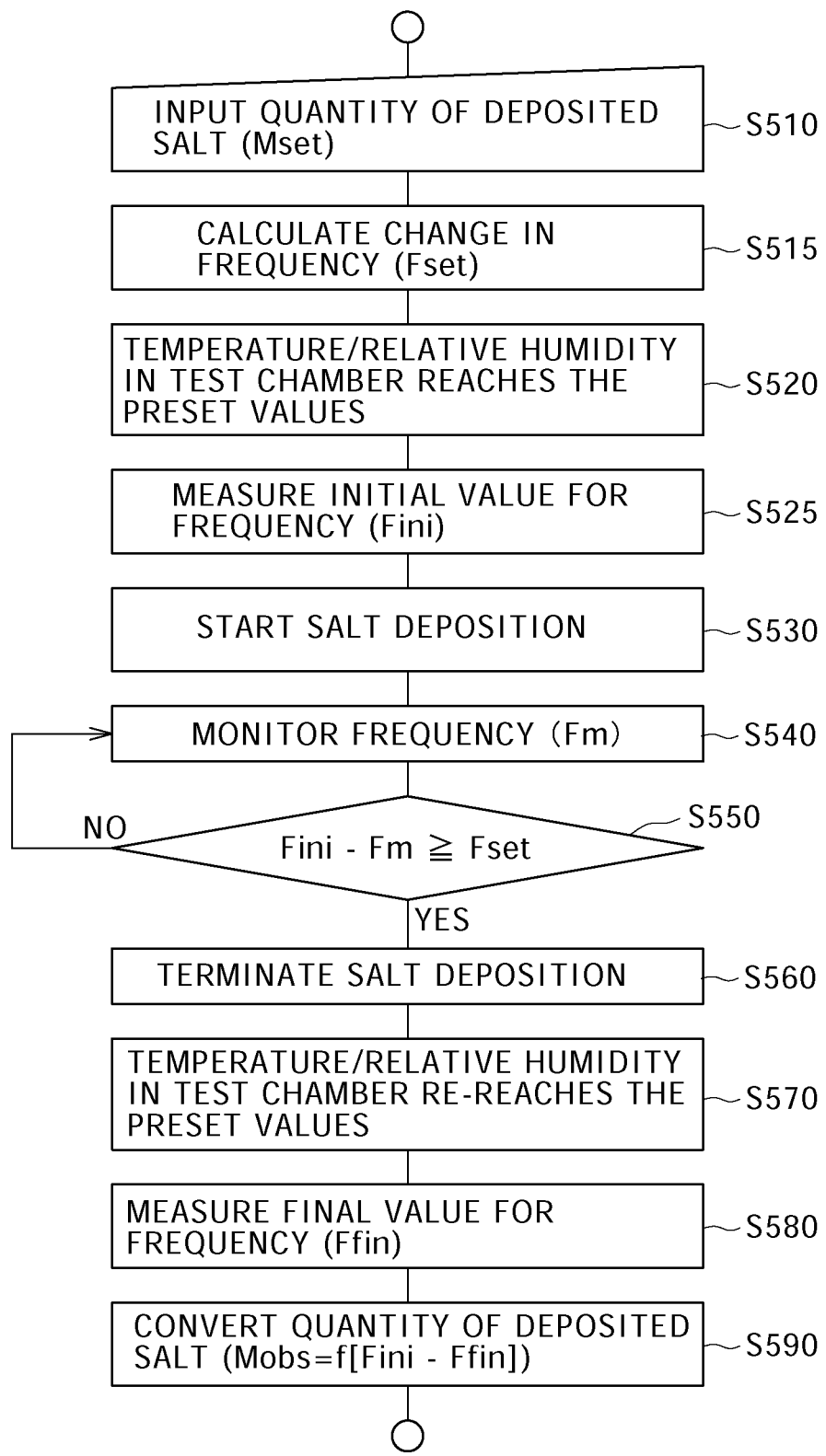
FIG. 6 is a flow sheet illustrating the steps of the atmospheric corrosion test procedure according to the embodiment 5 of the present invention.

FIG. 6 is a flow sheet illustrating the procedure for verifying the quantity of the salt content deposited on the surfaces of the test pieces using the test apparatus in the atmospheric corrosion test procedure of the present invention shown in FIG. 4.

In the salt deposition step, first, the quantity of deposited salt is entered in the control unit of the test apparatus. In this case, $M_{set}$ was set to 1 g/m² for the quantity of deposited salt content (S510). A change in frequency $F_{set}$ (Hz) on the quartz crystal microbalance sensor 190, which is equivalent to the quantity of the deposited salt content, is calculated (S515). In the actual step of depositing the salt content, when it is sensed that the temperature and relative humidity inside the thermo-humidistat chamber have reached 40° C. and 35%, respectively (S520), the initial value Fini (Hz) is measured (S525).

Then, the on-off valve 180 is opened to start the deposition of the salt content (S530). The measurement of the frequency $F_m$ on the quartz crystal microbalance sensor 190 is started concurrently with the start of the deposition of the salt content, the quantity of the deposited salt content is monitored (S540), and a variance in frequency is calculated by evaluating a formula $F_{ini}-F_m$ to determine whether the obtained value has reached the preset $F_{set}$ (Hz) (S550). When $F_{ini}-F_m$ reaches $F_{set}$, the on-off valve 180 is closed to end the deposition of the salt content (S560).

Subsequently, the temperature and relative humidity inside the thermo-humidistat chamber 110 is controlled back to a temperature of 40° C. and a relative humidity of 35%, respectively and when they reach the preset condition (S570), the frequency $F_{fin}$ (Hz) on the quartz crystal microbalance sensor 190 is measured (S580) and the quantity $M_{obs}$ of the salt content actually deposited on the surfaces of the test pieces 160 was converted based on the variance in frequency obtained by evaluating the formula $F_{nin}-F_{fin}$ (S590). Thus, the quantity of the salt content deposited on the surfaces of the test pieces was verified.

It was verified that repeating the procedure according to this embodiment enabled a variance in quantity of the deposited salt content to be suppressed among the salt spray steps, and the quantity of the actually deposited salt content to be confirmed, improving the reproducibility of the corrosion test.

What is claimed is:

1. An atmospheric corrosion test procedure comprising:
a salt deposition step of supplying salt content containing chloride ions on the surfaces of test pieces placed in a thermo-humidistat chamber; and
a subsequent dry-wet cyclic step, the dry-wet cyclic step including a dry sub-step of drying the surfaces of the test pieces in the thermo-humidistat chamber at a low relative humidity and a subsequent wet sub-step, in which the relative humidity in the thermo-humidistat chamber is set to higher value than that in the dry sub-step, the sub-steps being cycled, and
wherein the salt content is supplied by spraying salt water in the salt spray step, a first dry sub-step of repeated dry sub-steps is carried out between the salt deposition step and the first wet sub-step of the repeated wet sub-steps, an exhaust sub-step of removing the salt mist sprayed inside the thermo-humidistat chamber is carried out between the salt deposition step and the first dry sub-step, and the quantity of the deposited salt content is controlled by adjusting the quantity of the sprayed salt water.

2. The atmospheric corrosion test procedure according to claim 1, wherein the dry sub-step is started from the salt deposition step or the wet sub-step by varying stepwisely the temperature and relative humidity inside the thermo-humidistat chamber.

3. The atmospheric corrosion test procedure according to claim 1, wherein the quantity of the sprayed salt water is adjusted based on a value obtained from the measurement of the mass or volume of the salt water.

4. The atmospheric corrosion test procedure according to claim 1, wherein the mass or volume of the salt water is measured with time, and when the measured value reaches a preset value for mass or volume, control is performed to stop the spray.

5. The atmospheric corrosion test procedure according to claim 1, wherein the salt deposition step is carried out in a space retained in one of conditions combining a temperature selected from a range from 0° C. to 60° C. and a relative humidity selected from a range from 10 to 98%.

6. The atmospheric corrosion test procedure according to claim 1, wherein the salt deposition step and the subsequent dry-wet cyclic step are further repeated subsequently to the previous dry-wet cyclic step.

7. The atmospheric corrosion test procedure according to claim 6, wherein a rinsing step of removing the salt content deposited on the surfaces of the test pieces is further carried out between the dry-wet cyclic step and the subsequent salt spray step.

8. The atmospheric corrosion test procedure according to claim 6, wherein one cycle, in which each of the salt spray step and the dry-wet cyclic step is carried out once, is repeated everyday or at the intervals of one to six days.

9. The atmospheric corrosion test procedure according to claim 1, wherein the dry sub-step includes a mass measuring step of measuring the salt content remaining on the surfaces of the test pieces after the salt water is removed.

10. An atmospheric corrosion test apparatus comprising:
a thermo-humidistat chamber for placing test pieces;
a salt-water reservoir for storing salt water in the thermo-humidistat chamber;
a salt mist supplying unit for generating the salt water mist;
an exhaust unit for collecting and exhausting the mist from inside the thermo-humidistat chamber;
a flow rate measuring unit for measuring the quantity of the supplied mist or an deposited salt measuring unit for measuring the quantity of the salt-water deposited on the test pieces; and
a control unit for adjusting the quantity of the supplied mist based on a signal issued from the flow rate measuring unit or the deposited salt measuring unit.

11. The atmospheric corrosion test apparatus according to claim 10, further comprising:
a rinsing nozzle for spreading rinsing water onto the test pieces; and
a warm-air drying unit for removing the rinsing water deposited on the test pieces.

12. The atmospheric corrosion test apparatus according to claim 10, wherein the exhaust unit provides a function for varying stepwisely the temperature and relative humidity inside the thermo-humidistat chamber.

13. The atmospheric corrosion test apparatus according to claim 10, further comprising:
an on-off valve for adjusting the quantity of the supplied mist incorporated between the salt water reservoir and the salt mist generating unit.

14. The atmospheric corrosion test apparatus according to claim 13, wherein the control unit controls the on-off valve based on the signal issued from the deposited salt measuring unit.

* * * * *